United States Patent [19]

Bisset et al.

[11] 3,957,884
[45] May 18, 1976

[54] KETONE PEROXIDE PRODUCTION
[75] Inventors: Douglas M. Bisset, Sarnia; Colin Mercer, Port Lambton, both of Canada
[73] Assignee: Chinook Chemicals Corporation Limited, Toronto, Canada
[22] Filed: Sept. 12, 1973
[21] Appl. No.: 396,524

[52] U.S. Cl............................. 260/610 R; 252/186
[51] Int. Cl.² ........................................ C07C 179/06
[58] Field of Search .... 260/610 R, 610 SK, 610 SC, 260/610 D

[56] References Cited
UNITED STATES PATENTS

| 3,330,871 | 7/1967 | Mageli et al. | 260/610 SK |
| 3,692,841 | 9/1972 | McCloskey | 260/610 SC |

FOREIGN PATENTS OR APPLICATIONS

| 45-8412 | 3/1970 | Japan | 260/SK |

OTHER PUBLICATIONS

Sussman, "Industrial & Engr. Chem." Vol. 38 No. 12 pp. 1228–1230, (1946).

Primary Examiner—Joseph E. Evans
Assistant Examiner—W. B. Lone
Attorney, Agent, or Firm—Sim & McBurney

[57] ABSTRACT

Safe ketone peroxide compositions are provided utilizing a novel solvent system which boils smoothly over a wide range of temperatures. In addition, ketone peroxide compositions are prepared by reacting an excess of the ketone with hydrogen peroxide in a homogeneous system, followed by stripping excess ketone and water from the product.

20 Claims, 1 Drawing Figure

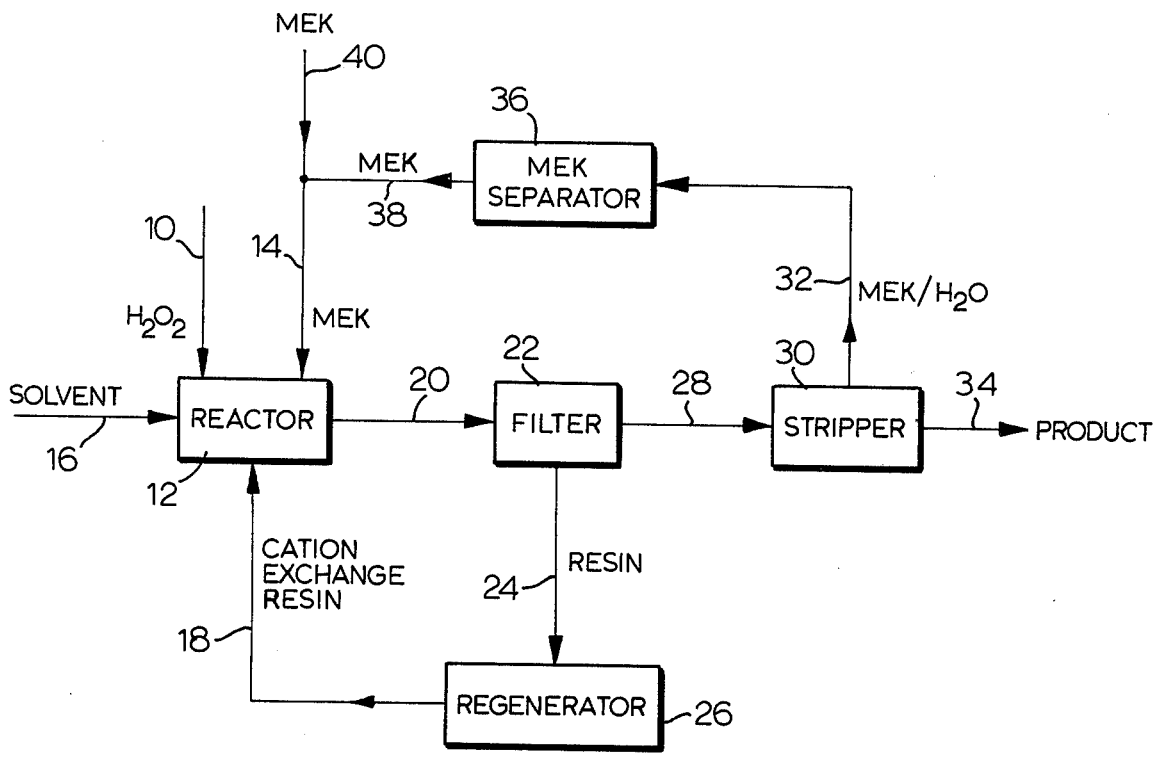

3,957,884

KETONE PEROXIDE PRODUCTION

FIELD OF INVENTION

The present invention is directed to ketone peroxide compositions, particularly "safe" ketone peroxide compositions, and to the preparation of ketone peroxide compositions.

BACKGROUND TO THE INVENTION

Ketone peroxides are extensively used for the initiation of polymerization of ethylenically unsaturated compounds. Peroxides, however, have a tendency to be inflammable and exlosive, with some exhibiting these properties to a greater extent than others. These properties carry with them obvious hazards to the users of the materials as well as to the manufacturers.

Many suggestions have been made to reduce the inflammability of ketone peroxides, as discussed in more detail below, usually involving the incorporation of large quantities of water in the composition, the use of various additives and the use of particular solvents.

The apparent need to provide compositions of this sort has led to the widespread adoption of particular procedures for preparing such ketones. A commonly used procedure involves reaction of an aliphatic ketone, typically methyl ethyl ketone, in a solvent system under acid conditions with an aqueous solution of hydrogen peroxide, resulting in a two phase system. An excess of hydrogen peroxide over the stoichiometry to form the ketone peroxide is used in order to react as much of the ketone as possible.

The aqueous phase is separated from the organic phase and usually is discarded. The discarded aqueous phase contains unreacted hydrogen peroxide and possibly some unreacted ketone, and hence the discard of the aqueous phase results in an uneconomic use of these materials.

The organic phase contains a substantial proportion of water, typically about 10 to 15%, and the presence of such large amounts of water has disadvantages associated mainly with the end use of the peroxide material, since the water generally is incompatible with the organic components to be polymerized. The presence of water leads to bubbling in polymeric thin film formation.

In addition, the use of aqueous acids results in residual acidity in the organic phase which promotes continued reaction of the peroxide to higher oligomers. The trimer and higher oligomers are known to impart explosive properties to the composition. Therefore, the acidity has been neutralized, but the presence of commonly-employed neutralizing agents provides surface problems for the products of polymerization initiated by the peroxides containing such agents.

The prior art procedures for the production of aliphatic ketone peroxides therefore suffer from several drawbacks, which are sought to be overcome by the process which constitutes one aspect of the present invention.

In one aspect of the present invention, there is provided a novel process for forming aliphatic ketone peroxides, resulting in a product having superior stability, improved utility and decreased hazard.

As previously indicated there have been a number of prior art suggestions to provide safe ketone compositions, such as is described in U.S. Pat. No. 3,330,871 wherein it is indicated that a class of "Safety Solvents" for the ketone peroxide may be used to provide compositions which exhibit resistance to ignition and once ignited burn mildly. A wide variety of solvents are mentioned including various gylcols. However, it has been found that, while the compositions provided in the manner disclosed in this patent do indeed exhibit some resistance to ignition and once ignitied burn mildly, after burning for a period of time, which may vary widely depending on the solvent used and the quantity present, the composition suddenly flares up and burns vigorously. The tendency of these prior art compositions to flare up suddenly is extremely hazardous to a user or manufacturer seeking to extinguish the ignited composition, since while the ignited composition may be burning mildly and the operator can approach the flame with suitable extinguishing equipment, before extinguishing the flame, a sudden flare up may occur, causing injury to the operator.

In the second aspect of the present invention, there is provided a safe acyclic ketone composition which exhibits considerable resistance to ignition and when ignited burns in a controlled manner until all the peroxide composition has been consumed. Thus, the present invention avoids the flare up problem attendant the prior art compositions of U.S. Pat. No. 3,330,871.

SUMMARY OF INVENTION

According to the process of the one aspect of the present invention, an alicyclic ketone and hydrogen peroxide are reacted in the presence of an insoluble cation exchange resin in a non-benzenoid solvent which is a solvent for the aliphatic ketone, the product ketone peroxide and water.

In complete contrast to prior art systems, an excess of the ketone is used, to ensure as complete reaction of the hydrogen peroxide as possible, the excess being at least 1.1, preferably about 1.1 to 1.6 times the stoichiometric requirement. Also in complete contrast to prior art practice, the solvent maintains a homogeneous liquid medium throughout the reaction. This latter step is possible because it is unnecessary in the present invention to separate and discard excess hydrogen peroxide, or to ensure complete reaction of the ketone in contrast to the prior art procedures discussed above.

In contrast to the common practice of using hydrochloric and sulphuric acids, the present invention uses a cation exchange resin, which is insoluble in the reaction components or solvent hence is readily separated from the reaction products at the coompletion of the reaction. The use of the cation exchange resin results in substantially no residual acid and hence the necessity to add neutralizers is avoided. In addition, the cation exchange resin assists in the removal of metal ions from the composition which otherwise may lead to decomposition of the peroxide product.

The resulting homogeneous solution of solvent, ketone peroxide, unreacted ketone and water is subjected to an evaporation operation under reduced pressure at a temperature well below the decomposition temperature of the ketone peroxide to strip the water and unreacted ketone from the solution as a mixture and to leave a solution of ketone peroxide in nonbenzenoid solvent having a low content of, preferably substantially free from, these components. The excess ketone distilled from the solution also assist in the removal of any unreacted hydrogen peroxide from the vapour produced by the distillation.

The cation exchange resin may be separated from the liquid phase, either before or after the stripping operation, typically by simple filtration. The presence of the cation exchange resin during the stripping operation has no adverse effect on the product and may assist in driving the reaction to completion.

The maximum water content of the product depends on the ketone peroxide concentration, and for very low ketone peroxide concentrations, the water content may exceed 35%. However, due to the deleterious effect of water in the product, as mentioned above, it is preferred to provide a water content less than about 5%, preferably from 0 to about 4%. The water content of the products may be determined readily by gas chromatographic techniques. This technique also may be used to determine the free ketone content of the product, which preferably, is as low as possible. The free ketone concentration of the product should be below a value which will substantially lower the flash point of the product, usually below about 0.5% and, preferably, from 0 to about 0.4%.

The product containing the preferred water content conforms to the so-called "Freezing Test". In the Freezing Test, the product is cooled to −50°C and then thawed. To pass this test, the product must remain mobile on lowering the temperature to −50°C and homogeneous on thawing.

When a conventional aliphatic ketone peroxide composition containing substantial quantities of water is cooled and subsequently thawed, freezing occurs on lowering the temperature, and a phase separation occurs on thawing which is extremely difficult to reverse and, additionally, following such phase separation, the composition becomes more susceptible to explosion.

Further, it has been observed that upon subjecting commercially-available peroxide compositions of low water content to the Freezing Test, the products solidified between 0°C and −5°C.

The product of the process of this invention has been found to have improved stability properties as compared to conventionally-produced ketone peroxide compositions, thereby providing a product which may be stored over long periods without substantial loss of activity and danger of instability if stored through cold weather.

The presence of the unreacted ketone in the product solution allows the water to be stripped off since the two form azeotropic mixtures. Therefore, the excess of ketone utilized in the process of the present invention serves a dual role, namely, to ensure the reaction of substantially all the hydrogen peroxide and to assist in the removal of the water from the product.

The stripped mixture of water and aliphatic ketone may be readily processed to recover the aliphatic ketone, which may be recycled for reuse. The process of the invention therefore is economic in its use of both the aliphatic ketone and the hydrogen peroxide, and in addition, is less polluting since aqueous peroxide solutions are not sewered.

The stripping operation, which is an essential step in the process of this invention, has multifold advantages including:

1. The quantity of water present in the final product may be substantially decreased to a very low level, the stability of the composition thereby being improved without an increase in flammability;

2. The quantity of volatile solvents is reduced, resulting in a higher flash point product, a low concentration of explosive vapours and a reduction in bubbling caused by the volatile solvents in polyester films and 3. The product does not separate into phases on cooling and thawing.

The solvent used in the process of the invention to maintain homogeneity in the aqueous phase throughout the reaction may be a single solvent or a mixture of solvents, more particularly the mixture of solvents used to provide the safe ketone peroxide composition of the second aspect of the invention.

Among the solvents which may be used are alkylene glycols, ethylene glycol monoalkyl ethers, diethylene glycol monoalkyl ethers, alkanols having 3 to 12 carbon atoms, cycloalkanols having 3 to 6 carbon atoms in the ring, and cyclic ether substituted alcohols.

Examples of such solvents are ethylene glycol, propylene glycol, dipropylene glycol, hexylene glycol, 1,4-butylene glycol, 2,3-butylene glycol, ethylene glycol monoethyl ether, butyl cellosolve, diethylene glycol monoethyl ether and butyl carbitol.

In accordance with the second aspect of the invention, a composition is provided which is a homogeneous solution of the acyclic ketone peroxide in a solvent system, the solution having a flash point of at least about 200°F. The solvent system and the individual solvents thereof essentially conform to several characteristics:

i. a mixture of solvents which boils smoothly over a wide range of temperatures, preferably at least 40°C and which commences to boil at a temperature of at least 175°C, the individual solvents having differing boiling points, preferably between about 200° and 300°C;

ii. a mixture of solvents which has a flash point of at least 200°F, preferably at least 220°F;

iii. a mixture of solvents which has an auto-ignition temperature of at least 225°C, preferably about 300° to 1000°C;

iv. a mixture of solvents which is a solvent for the ketone peroxide, water and free ketone, and additionally is compatible with the polymer system to be formed;

v. a mixture of solvents having low volatility;

vi. a mixture of solvents inert to the ketone and hydrogen peroxide reactants and product peroxide;

vii. a mixture of solvents which has low toxicity;

viii. a mixture of solvents which does not leave a solid residue after burning, which otherwise would result in after low;

ix. the individual solvents must be non-benzenoid;

x. the individual solvents must contain from 2 to 8 acyclic carbon atoms;

xi. the individual solvents should be inert and incapable of degradation under conditions of formation of the product to materials which may decompose the product peroxide;

xii. the individual solvents must be non-halogenated, and xiii. the individual solvents should be incapable of forming amine oxides.

Autoignition temperatures for various solvents and the determination thereof are described in an article entitled "Autoignition Temperatures of Organic Chemicals" by Carlos J. Hilads et al., Chemical Engineering, Sept. 4, 1972, pp 75 to 80. Autoignition is the lowest temperature at which a material begins to self-heat at a high enough rate to result in combustion.

By utilizing a mixture of solvents of differing boiling points and which boils smoothly over a wide temperature range, the heat of decomposition of the peroxide is used as heat of vaporization of the solvents and hence flare up due to decomposition of the aliphatic ketone peroxide is not possible.

The ketone peroxide composition provided in accordance with the second aspect of this invention, has been found to have excellent end use properties. For example, in spray coat applications where polyester gels of only a few thousandths of an inch thick, typically 10 to 15 thou, are provided, the product of the invention does not give rise to blisters or pin holes, in contrast to many commercially-available ketone peroxide formulations.

Additionally, it has been found that where tapered sections or sections of irregular thickness are cured from curable polyester materials in which the ketone peroxide composition of this invention is used as the polymerization initiator, this curing takes place uniformly throughout the thickness of the film. This result is of importance in particular in the fabrication of boats where the use of uneven thickness of polyester film is common.

As a result of this unexpected uniformity of curing, there is less laminate stress and lack of excessive localised heat build up. The stresses and heat build up can cause damage to the expensive molds used in the boat industry and hence should be avoided. In addition, bubbling caused by solvents is not observed in the polyester films.

A further result achieved in film formation initiated with the compositions of the invention is that when the cured article, such as a boat, is removed from the mold, the film is completely cured. In many conventional systems, the film is not completely cured upon removal from the mold.

Compositions in accordance with the present invention have improved solubility in diallyl phthalate, as compared to conventional commercially-available fire retardent ketone peroxide compositions. This property is important since diallyl phthalate is widely used as a cross-linking diluent in spray applications of ketone peroxides.

BRIEF DESCRIPTION OF DRAWING

The sole FIGURE of the drawing shows a schematic flow sheet of one embodiment of this invention.

DESCRIPTION OF PREFERRED EMBODIMENT

The acyclic ketone which is formed into a peroxide by the process of the present invention and into the peroxide derivatives of which may be present in the composition of the present invention are acyclic ketones of the formula R—CO—R', where R and R' each are straight or branched chain alkyl groups in which the total number of carbon atoms in R and R' is from 3 to 6.

Suitable ketones include diethyl ketone, methyl ethyl ketone (MEK), methyl propyl ketone and methyl isobutyl ketone.

The ketone most commonly employed to form ketone peroxides is methyl ethyl ketone and this particular material is preferred in both aspects of the present invention. The invention will be described hereinafter with particular reference to this ketone.

Referring to the drawing, hydrogen peroxide, typically as an aqueous solution thereof containing 50% $H_2O_2$, is fed by line 10 to a reactor 12 containing methyl ethyl ketone fed by line 14 and solvent fed by line 16. A cation exchange resin in hydrogen ion form, fed by line 18 generally in the form of beads and insoluble in the reactants or the solvent, also is present in the reactor 12. The hydrogen peroxide generally is added dropwise to the solution to react with the methyl ethyl ketone and the reaction may be continued after completion of addition of the hydrogen peroxide.

The quantity of methyl ethyl ketone fed by line 14 is at least 1.1 times the stoichiometric quantity required to react with the hydrogen peroxide fed by line 10. Typically the amount is at least 1.5 times the weight of the hydrogen peroxide solution fed by line 10.

The solvent fed by line 16 preferably is one conforming to the requirements of the solvent system used in the second aspect of the invention. Each of the solvents may contain from 2 to 6 acyclic carbon atoms.

Typical mixtures which may be used to provide the solvent system, especially with methyl ethyl ketone peroxide, include various mixtures of C2 to C6 glycols and C3 to C6 trialkyl phosphates, for example, mixtures of numbers of the following materials:

|  | Boiling Point°C. | Flash Point°F |
|---|---|---|
| Ethylene Glycol | 197.2 | 240.8 |
| Diethylene Glycol | 245.0 | 290 |
| Dipropylene Glycol | 233 | 330 |
| Hexylene Glycol | 198 | 230 |
| Triethyl phosphate | 216 | 240 |

Crude ethylene glycol, usually containing quantities of diethylene glycol and triethylene glycol, may be used in the solvent system fed by line 16. Glycol derivatives such as ethylene glycol acetate, may be used in the solvent system.

The relative proportions of the solvents, their number, and the difference between their individual boiling points in the solvent system may vary widely and are a matter of choice, provided that the overall composition and the individual components conform to the above-described parameters.

Where other solvents are fed by line 16, such solvents should be non-benzenoid, non-toxic, compatible with and inert to the peroxide product, peroxide reactant, water and the hydrogen peroxide and generally oxygenated.

The quantity of solvent fed by line 16 should be at least sufficient to maintain a homogeneous reaction mixture throughout the addition of hydrogen peroxide.

The reaction is carried out at as low a temperature as possible compatible with speed of reaction. Higher temperatures favour decomposition of the product, whereas low temperatures below 10°C result in long reaction times. The process is carried out at a temperature below about 35°C, preferably between about 20° to 30°C, with reaction times from about 1 to 2 hours.

Following completion of the reaction of the hydrogen peroxide with the methyl ethyl ketone there is obtained a homogeneous solution of solvent, product ketone peroxide, water and unreacted methyl ethyl ketone in admixture with resin. The admixture is passed by line 20 to a filter 22 wherein the solid resin is filtered from the homogeneous solution. Alternatively, the resin may be separated after the next processing step.

The recovered resin is passed by line 24 to a regenerator 26 prior to recycle of regenerated cation exchange resin to the reactor 12 by line 18.

The filtered solution then is passed by line 28 to a stripper 30 wherein the solution is heated under reduced pressure to remove an azeotrope of methyl ethyl ketone and water. While three separate units, namely reactor 12, filter 22 and stripper 30 are described, this is for ease of illustration of the process of the invention, and the three operations may be carried out in a single vessel.

The stripper 30 generally is maintained under a vacuum in order to lower the stripping temperature and hence reduce the danger of decomposition of the ketone peroxide. The temperature of operation of the stripper 30 generally is less than about 40°C with the applied vacuum being as high as possible. The excess methyl ethyl ketone and water are removed from the homogeneous system in the stripper 30 by line 32. The stripping usually is continued until no further material can be stripped from the product, and usually is complete in less than 4 hours, usually about 1 hour.

The resulting solution of methyl ethyl ketone peroxide in solvent in line 34 is substantially free from unreacted methyl ethyl ketone and free water, and passes the Freezing Test mentioned above.

The concentration of the ketone peroxide in the product in line 34 may be in excess of the industry standard of 11% active oxygen, in which case the product may be diluted with further amounts of solvent, either during the stripping operation or thereafter, to provide the required active oxygen value.

The active oxygen content of the final composition may vary widely, typically from 0.1 to 13% AO, with varying quantities of solvent being employed, typically from 5 to 90% of the composition.

The material in line 32 may be passed to a separator 36 wherein the methyl ethyl ketone is separated and forwarded by line 38 to mix with further methyl ethyl ketone fed by line 40 to provide the methyl ethyl ketone feed in line 14.

By utilizing an excess of methyl ethyl ketone there is realized an economic utilization of hydrogen peroxide, and since the excess is recovered for recycling, hence, there is also economic utilization of ketone.

EXAMPLES

The invention is illustrated further by the following Examples:

EXAMPLE I

A mixture of solvents consisting of 7.38 lbs of triethyl phosphate, 2.62 lbs of ethylene glycol, 2.62 lbs of diethylene glycol and 2.62 lbs of dipropylene glycol was charged to a reaction vessel and 66.5 lbs of methyl ethyl ketone was added. 1.36 lbs of Dowex 50 W-X8 cation exchange resin in hydrogen ion form was added to the solution in the reaction vessel.

The mixture of solvents charged to the reaction vessel was found to commence boiling at 179.5°C and to boil smoothly to dryness over an increasing temperature range to 224.0°C.

41.6 lbs. of 50% aqueous solution of hydrogen peroxide was added slowly with stirring over a 45 minute period, with the temperature being controlled by cooling below about 88°F. The resulting mixture was allowed to react, with stirring and agitation by nitrogen gas bubbled through, for a further 75 minutes.

The liquid in the reaction vessel remained homogeneous thoughout the reaction and then was cooled to ambient temperature prior to filtration of the cation exchange resin therefrom.

Under a vacuum of approximately 27 inches mercury, the filtrate was stripped of water and unreacted methyl ethyl ketone over a period of about 3½ hours at a rising temperature between 70° and 116°F.

41.2 lbs of stripped material was recovered and 70 lbs of methyl ethyl ketone peroxide solution was obtained. The product was very difficult to ignite, and when ignited burned with a controlled flame until all the liquid was consumed.

In addition, the product was subjected to the Freeze Test and the liquid remained mobile on cooling to −50°C and did not exhibit phase separation on cooling and thawing.

The product had an active oxygen content of about 11.5% and samples after storage for 183 days under laboratory conditions in which the temperature ranged from 50° to 95°F, mainly 65° to 75°F exhibited an active oxygen content of 11.2%, thereby indicating the stability of the product.

In similar storage tests when exposed to outdoor weather conditions in which the temperature ranged from −5°F to 80°F (shade temperature), the active oxygen content of the product after 148 days was 7.4%, while comparative samples of Aposet 720 and FR222 had exploded by that time.

EXAMPLE II

A two-gram sample of the product of Example 1 was placed in a small aluminum dish 12.5 mm high by 44 mm diameter. Similar two-gram samples of commercially-available peroxide compositions known as DNF (Wallace & Tiernan and formulated in accordance with U.S. Pat. No. 3,330,871) and Aposet 720 (M and T) were placed in similar dishes.

A ¾ inch flame from a small pilot burner was adjusted to impinge the liquid surface at about a 60° angle. The flame was removed on ignition of the sample. The times to ignition were recorded for a number of samples and the average times are reproduced in the Table 1:

TABLE I

| | |
|---|---|
| Example 1 | 71 secs. |
| DNF | 68 secs. |
| Aposet 720 | 25 secs. |

Total burning times varied within samples of each product and a true comparison in this regard was not possible. The product of Example 1 burned mildly until all the peroxide had been consumed. On the other hand the DNF burned mildly for a short time before buring very vigorously.

A sample product formed from methyl ethyl ketone and hydrogen peroxide in ethylene glycol burned very readily.

EXAMPLE III 72.0 lbs of methyl ethyl ketone, 16.50 lbs of hexylene glycol and 1.3 lbs of Amberlite 1R120 cation exchange resin in hydrogen ion form were charged to a glass reactor fitted with a reflux condenser, an external jacket for heating or cooling and an agitator.

45.04 lbs of a 50% aqueous solution of hydrogen peroxide was added slowly with stirring while the mixture was maintained by cooling at a temperature of above 70° to 88°F. When addition of hydrogen peroxide was complete, the reaction was allowed to proceed for a further 75 minutes.

The liquid in the reaction vessel remained homogeneous throughout the reaction and then was cooled to ambient temperature prior to filtration of the cation exchange resin therefrom.

The mixture thereafter was subjected to vacuum distillation at a temperature ranging from 88°F initially to 116°F at the end while the pressure changed from 100 mm mercury to 54 mm mercury from the beginning to the end, which was after 255 minutes of reaction. The product 78 lbs of peroxide contained 11.5% active oxygen.

Modifications are possible within the scope of the invention.

What we claim is:

1. In a process for the production of an acyclic ketone peroxide which comprises reacting at a temperature below about 35°C (a) an acyclic ketone of the formula R—CO—R' where R and R' each are straight or branched chain alkyl groups in which the total number of carbon atoms is from 3 to 6 and (b) hydrogen peroxide in the presence of a cation exchange resin in the hydrogen form and separating the cation exchange resin after completion of said reaction, the improvement which comprises:
   i. carrying out said reaction in at least one nonbenzenoid inert solvent, said solvent being a solvent for water, the aliphatic ketone and the ketone peroxide,
   ii. the quantity of acyclic ketone being at least 1.1 times the molar stoichiometric amount to produce the acyclic ketone peroxide,
   iii. the quantity of said solvent being sufficient to maintain a homogeneous reaction medium throughout the reaction and to obtain from said reaction a homogeneous system of said solvent, acyclic ketone peroxide, unreacted acyclic ketone and water, and
   iv. stripping water and unreacted acyclic ketone from said homogeneous system by boiling said homogeneous system at a temperature below about 40°C under a vacuum.

2. The process of claim 1 wherein said at least one non-benzenoid inert solvent is provided by at least one solvent selected from the group consisting of alkylene glycols, ethylene glycol monoalkyl ethers, diethylene glycol monoalkyl ethers, alkanols having from 3 to 12 carbon atoms, cycloalkanols having from 3 to 6 carbon atoms in the ring and cyclic ether substituted alcohols.

3. In a process for the production of an acyclic ketone peroxide which comprises reacting at a temperature below about 35°C (a) an acyclic ketone of the formula R—CO—R' where R and R' each are straight or branched chain alkyl groups in which the total number of carbon atoms is from 3 to 6 and (b) hydrogen peroxide in the presence of a cation exchange resin in the hydrogen form and separating the cation exchange resin after completion of said reaction, the improvement which comprises:
   i. carrying out said reaction in at least one nonbenzenoid solvent, said solvent being a solvent for water, the aliphatic ketone and the ketone peroxide and selected from the group consisting of ethylene glycol, propylene glycol, dipropylene glycol, hexylene glycol, 1,4-butylene glycol, 2,3-butylene glycol, ethylene glycol monoethyl ether, butyl cellosolve, diethylene glycol monoethyl ether and butyl carbitol,
   ii. the quantity of acyclic ketone being at least 1.1 times the molar stoichiometric amount to produce the acyclic ketone peroxide,
   iii. the quantity of said solvent being sufficient to maintain a homogeneous reaction medium throughout the reaction and to obtain from said reaction a homogeneous system of said solvent, acyclic ketone peroxide, unreacted acyclic ketone and water, and
   iv. stripping water and unreacted ketone from said homogeneous system by boiling said homogeneous system at a temperature below about 40°C under a vacuum.

4. The process of claim 3 wherein said stripping step is continued until the resulting solution of acyclic ketone peroxide in said solvent has an unreacted ketone content less than about 0.5% and a water content less than about 5%.

5. The process of claim 3 wherein said stripping is carried out until the product contains from 0 to about 0.4% of unreacted ketone and from 0 to about 4% of water.

6. The process of claim 3 wherein said acyclic ketone is methyl ethyl ketone.

7. The process of claim 3 wherein said quantity of acyclic ketone is about 1.1 to about 1.6 times the molar stoichiometric amount necessary to produce the acyclic ketone peroxide.

8. The process of claim 3 wherein said quantity of acyclic ketone is about 1.5 times the molar stoichiometric amount necessary to produce the acyclic ketone peroxide.

9. The process of claim 3 wherein said reaction takes place at a temperature of about 20° to 30°C for about 1 to 2 hours.

10. The process of claim 1 including altering the solvent proportion of said resulting solution to provide an active oxygen content of about 11%.

11. The process of claim 3 including recovering unreacted acyclic ketone from the material and utilizing said recovered acyclic ketone to react with further hydrogen peroxide.

12. The process of claim 3 wherein said cation exchange resin is separated from said homogeneous system prior to said stripping step.

13. The process of claim 3 wherein said cation exchange resin is separated from said homogeneous system after said stripping step.

14. In a process for the production of an acyclic ketone peroxide which comprises reacting at a temperature below about 35°C (a) an acyclic ketone of the formula R—CO—R' where R and R' each are straight or branched chain alkyl groups in which the total number of carbon atoms is from 3 to 6 and (b) hydrogen peroxide in the presence of a cation exchange resin in the hydrogen form, separating the cation exchange resin after completion of said reaction and recovering the ketone peroxide, the improvement which comprises:
   a. carrying out said reaction in a solvent system which is a solvent for water, the aliphatic ketone and the ketone peroxide, said solvent system consisting of a mixture of solvents which boils smoothly over a wide range of temperatures and which commences to boil at a temperature of at least 175°C, having a flash point of at least 200°F and an autoignition temperature of at least 225°C, said mixture having a low volatility, low toxicity and being a solvent for and inert to the ketone peroxide, said mixture of solvents being incapable of leaving a solid residue after burning, the individual solvents of said mixture being non-benzenoid, non-halogenated and incapable of forming amine oxides and containing from 2 to 8 acyclic carbon atoms, and having differing boiling points, b. the quantity of said solvent system being sufficient to maintain a homogeneous reaction medium throughout the reaction and to obtain from the reaction a homogeneous system of solvent, acyclic ketone peroxide, unreacted acyclic ketone and water;

c. the quantity of acyclic ketone being at least 1.1 times the molar stoichiometric amount to produce the acyclic ketone peroxide; and d. stripping water and unreacted acyclic ketone from said homogeneous system by boiling said homogeneous system at a temperature below about 40°C under a vacuum.

15. The process of claim 14 wherein said individual solvents have differing boiling points between about 200° and 300°C.

16. In a process for the production of an acyclic ketone peroxide which comprises reacting at a temperature below about 35°C (a) an acyclic ketone of the formula R—CO—R' where R and R' each are straight or branched chain alkyl groups in which the total number of carbon atoms is from 3 to 6 and (b) hydrogen peroxide in the presence of a cation exchange resin in the hydrogen form, separating the cation exchange resin after completion of said reaction and recovering the ketone peroxide, the improvement which comprises:

a. carrying out said reaction in a solvent system which is a solvent for water, the aliphatic ketone and the ketone peroxide, said solvent system consisting of a mixture of solvents which boils smoothly over a wide range of temperatures and which commences to boil at a temperature of at least 175°C, having a flash point of at least 200°F and an autoignition temperature of at least 225°C, said mixture having a low volatility, low toxicity and being a solvent for an inert to the ketone peroxide, said mixture of solvents being incapable of leaving a solid residue after burning, the individual solvents of said mixture being non-benzenoid, non-halogenated and incapable of forming amine oxides and containing from 2 to 8 acyclic carbon atoms, and having differing boiling points, said individual solvents being selected from C2 to C6 glycols and C3 to C6 trialkyl phosphates;

b. the quantity of said solvent system being sufficient to maintain a homogeneous reaction medium throughout the reaction and to obtain from the reaction a homogeneous system of solvent, acyclic ketone peroxide, unreacted acyclic ketone and water;

c. the quantity of acyclic ketone being at least 1.1 times the molar stoichiometric amount to produce the acyclic ketone peroxide; and d. stripping water and unreacted acyclic ketone from said hommogeneous system by boiling said homogeneous system at a temperature below about 40°C under a vacuum.

17. The process of claim 14 wherein said solvent system boils smoothly over an at least 40°C temperature range.

18. The process of claim 14 wherein said mixture has a flash point of at least 220°F.

19. The process of claim 14 wherein said mixture has an autoignition temperature of about 300° to 1000°C.

20. The process of claim 16 wherein said individual solvents are selected from ethylene glycol, diethylene glycol, dipropylene glycol, hexylene glycol and triethyl phosphate.

* * * * *